United States Patent
Wang et al.

(10) Patent No.: US 9,629,787 B2
(45) Date of Patent: Apr. 25, 2017

(54) PREPARATION METHOD AND USE OF N-ACYL ACIDIC AMINO ACID OR SALT THEREOF

(71) Applicant: NANJING HUASHI CHEMICAL CO., LTD, Jiangsu (CN)

(72) Inventors: Changguo Wang, Nanjing (CN); Xianglan Chen, Nanjing (CN); Baoyong Li, Nanjing (CN)

(73) Assignees: Nanjing Huashi New Material Co., Ltd., Nanjing (CN); Sino Lion USA LLC, Florham Park, NJ (US)

( * ) Notice: Subject to any disclaimer, the term of this patent is extended or adjusted under 35 U.S.C. 154(b) by 0 days.

(21) Appl. No.: 14/913,113

(22) PCT Filed: Apr. 4, 2014

(86) PCT No.: PCT/CN2014/074812
§ 371 (c)(1),
(2) Date: Feb. 19, 2016

(87) PCT Pub. No.: WO2015/024385
PCT Pub. Date: Feb. 26, 2015

(65) Prior Publication Data
US 2016/0200668 A1    Jul. 14, 2016

(30) Foreign Application Priority Data
Aug. 21, 2013  (CN) .......................... 2013 1 0366015

(51) Int. Cl.
*A61K 8/44*  (2006.01)
*A61Q 19/10*  (2006.01)
*C07C 231/02*  (2006.01)

(52) U.S. Cl.
CPC ................ *A61K 8/44* (2013.01); *A61Q 19/10* (2013.01); *C07C 231/02* (2013.01)

(58) Field of Classification Search
CPC ......... A61K 8/44; C07C 231/02; A61Q 19/10
See application file for complete search history.

(56) References Cited

U.S. PATENT DOCUMENTS 6,060,613 A * 5/2000 Hattori .................. C07C 231/02
554/68
9,187,407 B2 * 11/2015 Koshti ................... C07C 51/60

FOREIGN PATENT DOCUMENTS

| CN | 1332721 A | 1/2002 |
|---|---|---|
| CN | 102126984 A | 7/2011 |
| CN | 103435509 A | 12/2014 |

* cited by examiner

*Primary Examiner* — Shailendra Kumar
(74) *Attorney, Agent, or Firm* — Fox Rothschild LLP

(57) ABSTRACT

The invention provides a preparation method of N-acyl acidic amino acid or a salt thereof, comprising subjecting a fatty acyl chloride and an amino acid to an amidation reaction under an alkaline condition. The preparation method is characterized in that in the amidation reaction, water is used as a solvent, an acidic amino acid or a salt thereof is used as a main raw material and a small amount of a neutral amino acid or a salt thereof is used as an auxiliary raw material, and the method comprises the following steps: under a stirring condition, firstly adding the fatty acyl chloride dropwise into an aqueous solution of the acidic amino acid or the salt thereof; adding an alkali to adjust the pH value of the reaction solution; after a certain amount of fatty acyl chloride having been added dropwise, adding an aqueous solution of the neutral amino acid or the salt thereof, and continuing to add the fatty acyl chloride dropwise until the addition is finished and stirring to maintain the reaction. The preparation method uses the reaction of the mixed amino acids and the fatty acyl chloride under a water-phase system, so that the conversion rates of the amino acids and the acyl chloride can be remarkably increased and the amount of residual amino acids is greatly reduced. The product can be directly used as a surfactant after simple post-treatment, and thus the cost is greatly reduced.

9 Claims, No Drawings

PREPARATION METHOD AND USE OF N-ACYL ACIDIC AMINO ACID OR SALT THEREOF

CROSS-REFERENCE TO RELATED APPLICATIONS

The present application is a U.S. national phase application of International Application No. PCT/CN2014/074812, filed Apr. 4, 2014, which in turn claims priority to Chinese Patent Application No. 201310366015.5, filed Aug. 21, 2013. The disclosures of both applications are hereby incorporated by reference in their entireties.

TECHNICAL FIELD

This patent relates to a surfactant of N-acyl acidic amino acid or a salt thereof, and in particular, to a preparation method of N-acyl acidic amino acid or salt thereof, which is a low cost method for preparing fatty acyl amino acid surfactants; and to the application of the N-acyl acidic amino acid prepared by such method.

BACKGROUND

N-acyl acidic amino acid or salt thereof is a kind of compound prepared from acylated amino acid. Typically, it is made by condensing fatty acid chloride and amino acid. Such kind of compound has good surface activity, foaming performance, cleaning performance and mildness, and therefore, it is widely used in cosmetics, personal care cleansing products, and meanwhile, it also has a wide range of application in other fields, such as food additives, metal machining, ore floatation, oil and gas mining, as well as agriculture, biological products and pharmaceutical preparation.

N-acyl acidic amino acid or salt thereof is a compound made by acylating such acidic amino acids as glutamic acid and aspartic acid, such that it embodies higher performance than acylated neutral amino acid products. Glutamic acid surfactants have better application characteristics than neutral amino acid surfactants, such as better foams, suitability to be used in weakly acidic system, matching with human skin pH, and even less irritation, etc. Typically, N-acyl acidic amino acid or salt thereof are made by condensing fatty acid chloride and amino acid. Such production process uses a lot of solvents, such as polar solvents as acetone, methyl ethyl ketone, dioxane, tetrahydrofuran, etc. In the present industrial production, water has already been used as solvent for the neutral amino acid surfactants, such that it can substantially reduce cost. Such products have already been widely used. However, when water is used as solvent in the condensation reaction of acidic amino acid with fatty acid chloride, the conversion ratio is relative low, normally 70%. In addition, such products have low quality, and subject to complicated post treatment. In actual production, it often uses polar organic solvents, such that the conversion ratio can be substantially increased to 85% to 90%. But it has the problem of complicated post treatment and increased cost, which makes it difficult to be used as widely as neutral amino acid surfactants.

U.S. Pat. No. 6,008,390 discloses that in the water-phase reaction system, conversion ratio of glutamic acid can be increased to about 85% with high power agitator. But this process causes power consumption to increase substantially. In addition, it is very difficult to enlarge large scale industrialized production equipment. High speed agitator may also produce too much foam, which reduces reaction and mixing effect. All these factors undoubtedly bring difficulty to production and increase production cost, and therefore hinder the market application. In addition, in the above preparation process, too much excess amount of glutamic acid, high cost, and residual amino acid in the product all bring problems to the usage.

SUMMARY

With respect to defaults existing in the prior art production process of N-acyl acidic amino acid, the invention provides a preparation method of N-acyl acidic amino acid or a salt thereof, which uses the reaction of the mixed amino acid and the acyl chloride under a water-phase system. The preparation method uses an acidic amino acid as a main raw material, and uses a small amount of neutral amino acid as an auxiliary raw material. Reacting with the acyl chloride under a water-phase system may remarkably increase the conversion rates of the amino acid and the acyl chloride, and greatly reduce the amount of residual amino acids. The product can be directly used after being treated simply, and thus the cost is greatly reduced.

In order to achieve the above-mentioned purpose, the invention adopts the following technical scheme:

A preparation method of N-acyl acidic amino acid or salt thereof, comprising: subjecting a fatty acyl chloride and an amino acid to an amidation reaction under an alkaline condition, characterized in that, the amidation reaction uses water as a solvent, an acidic amino acid or a salt thereof as a main raw material, and a small amount of a neutral amino acid or a salt thereof as an auxiliary raw material; under a stirring condition, firstly adding the fatty acyl chloride dropwise into an aqueous solution of the acidic amino acid or the salt thereof; adding an alkali to adjust the pH value of the reaction solution; after a certain amount of fatty acyl chloride having been added dropwise, adding an aqueous solution of the neutral amino acid or the salt thereof, and continuing to add the fatty acyl chloride dropwise until the addition is finished and stirring to maintain the reaction.

The method herein uses a mixture of acidic amino acid and a small amount of neutral amino acid, and subjects the mixture and acyl chloride to a reaction with water as a solvent, such that a desirable conversion rate may be obtained. As the product can be directly used after being simply treated, the cost is remarkably reduced than the previous reported methods.

In the preparation method herein, the molar ratio of the acidic amino acid versus the fatty acyl chloride versus the neutral amino acid is typically 0.6-1.3:1:0.01-0.5, preferably 0.7-1.2:1:0.05-0.4, and most preferably 0.8-1.0:1:0.1-0.3.

In the method, the neutral amino acid is added when the added fatty acyl chloride reaches 40% to 100% of its total amount, preferably 60% to 100%.

In the method, the pH of the reaction solution is maintained at 9 to 14, preferably at 10 to 11.

In the method, the reaction temperature is 5° C. to 50° C., preferably 15° C. to 30° C.

The invention uses industrially popular Schotten-Baumann condensation method, wherein under an alkaline condition, subjecting a fatty acyl chloride and an amino acid to a reaction to obtain N-acyl amino acid, and then adding acid to neutralize to obtain N-acyl amino acid. The fatty acyl chloride and amino acid are reacted under the alkaline condition, wherein an alkaline solution is used to adjust the pH value of the reaction solution, the said alkaline is generally selected from alkali metal hydroxides, ammonium or alkali metal salts, including but not limited to lithium hydroxide, potassium hydroxide, sodium hydroxide, sodium carbonate, potassium carbonate, ammonium carbonate, ammonium hydroxide, preferably lithium hydroxide, potassium hydroxide.

The carbon chain length of the said fatty acyl chloride is C6 to C22, or any combination thereof. The fatty acyl chloride is prepared by known methods from a fatty acid, wherein the carbon chain length of the fatty acid is C6 to 22, and wherein the substituents include linear and branched hydrocarbon group, saturated and/or with mono- or poly-double bond. Mono fatty acid or mixed acid may be used to prepare the fatty acyl chloride. The fatty acid includes, but not limited to, C6 to C22 saturated fatty acid, oleic acid, linolic acid, linolenic acid, isocaprylic acid, isostearic acid, coconut oil fatty acid, palmitoleic acid, soya oil acid, erucic acid, etc., preferably C8 to C22 fatty acid, more preferably C8 to C18 fatty acid.

The acidic amino acid herein refers to aspartic acid, glutamic acid, and the neutral amino acid includes sarcosine, glycine, lactamic acid, valine, leucine, isoleucine, proline, phenylalanine, tryptophane, methionine, serine, threonine, cysteine, tyrosine, asparaginate, and glutamine.

The invention also relates to the application of N-acyl acidic amino acid or salt thereof prepared by the above method as a surfactant.

For the sake of clarity, the following description takes an acidic amino acid as example, but the invention is not limited to this.

Preparation process of acyl glutamate typically adds an acyl chloride dropwise to a solution of glutamate. At early stage of the reaction, the glutamate is greatly excess with respect to the acyl chloride in the reaction system, with a difference of 10 to $10^2$ order of magnitude, such that the glutamate can be better converted to acyl glutamate. However, as the reaction proceeded, the molar ratio between glutamate and the acyl chloride in the system decreases, and concentration of the acyl chloride even exceeds that of the glutamate, such that the reaction proceeds very slowly at this time. However, as hydrolysis subsidiary reaction of the acyl chloride continues, if the acyl chloride cannot react rapidly with amino acid, then it will hydrolyze to a carboxylic acid and a salt. As such, conversion rate of the system is low, the acyl chloride is hydrolyzed to a fatty acid, and there are a lot of residual raw materials in the product. On one hand, it is very extravagant, while on the other hand, product performance is compromised, and even unavailable to be used.

Comparing to a neutral amino acid, such as glycine, sarcosine, the glutamic acid and the acyl chloride react slowly because that due to the two carboxyl groups in the molecular structure, which are strong electron-withdrawing groups, it is not favorable for the acylation reaction of Schotten-Baumann; and meanwhile, the two carboxyl groups in the acidic amino acid have large steric hindrance, which hinders the amidation reaction. The neutral amino acid does not have such unfavorable factor and it can react rapidly. With such difference, the invention employs acidic amino acid such as glutamic acid in combination with neutral amino acid to avoid the above problem.

The invention is mainly characterized in that, at the late stage of the reaction of the glutamic acid and the fatty acyl chloride, adding the neutral amino acid such as glycine therein effectively makes the remaining fatty acyl chloride react completely, in order to solve the problem of hydrolysis side reaction of the fatty acyl chloride. Meanwhile, the glutamic acid does not need to be in much excess to the acyl chloride, or even does not need to be in excess, such that residue concentration of the glutamic acid in the product is relatively low. The prepared N-acyl acidic amino acid or salt thereof can be used directly as the final product after being filtered simply. The production cost is remarkably reduced than that reported; and the product quality is satisfactory.

The N-acyl acidic amino acid or salt thereof provided by the invention can be directly used as a primary or secondary surfactant in personal care products, such as facial cleanser, bath wash, shower gel, toothpaste, shampoo, cleansing soap, etc., and as a surfactant in the industrial field. It may also be used as an intermediate, which may be prepared as a product with the expected characteristics after being refined, dried or subjected to derivatization reaction.

The low cost preparation method of N-acyl acidic amino acid surfactant herein uses a mixture of an acidic amino acid and a small amount of neutral amino acid, and subject such mixture and a fatty acyl chloride to a reaction by using water as a solvent, in order to obtain a satisfactory conversion rate, wherein the molar ratio of the acidic amino acid to the acyl chloride decreases remarkably, from 1.2-1.3:1, to 0.8-1.0:1, and the residual acidic amino acid in the product decreases at least 50% than that in U.S. Pat. No. 6,008,390 method. The product can be directly used after simple post-treatment. Production cost of the N-acyl acidic amino acid surfactant produced by the method herein decreases 50%, such that it suits to the industrialized production.

DETAILED DESCRIPTION

The technical schemes described in the application are further described in detail through the following embodiments. However, it is necessary to point out that, the following embodiments are only used to describe the invention, but not to limit the scope of protection of the invention.

Example 1

Preparation of Sodium Cocoyl Glutamate

Place 290 g sodium glutamate aqueous solution in a reactor (25% sodium glutamate, pH value: 12, temperature: 20° C.); add 110 g coconut acid chloride in a dropping funnel, wherein the molar ratio of the acyl chloride to the glutamate is 1:0.9. Slowly add the acyl chloride solution dropwise, and use 30% sodium hydroxide solution to adjust the pH value of the material in the reactor and maintain the pH value at 10 to 11. After the acyl chloride is added dropwise to 90% of the total amount, immediately add 70 g sodium glycinate aqueous solution with a concentration of 14.6%, wherein the molar ratio of the sodium glycinate to the acyl chloride is 0.2:1; and then slowly increase the reaction temperature to 25-30° C. and maintain such temperature for 1 h. After the reaction is complete, the product is clear and transparent. The concentration of free fatty acid salt in the product is measured at 2.9% with HPLC, and the conversion rate is calculated as 85% by the acyl chloride.

Comparative Example 2

Preparation of Sodium Cocoyl Glutamate

Place 290 g sodium glutamate aqueous solution in a reactor (25% sodium glutamate, pH value: 12, temperature: 20° C.). Add 89 g coconut acid chloride in a dropping funnel. Slowly add the acyl chloride dropwise, and use 30% sodium hydroxide solution to adjust the pH value of the material in the reactor and maintain the pH value at 10 to 11.

After the acyl chloride is added dropwise to completion, slowly increase the reaction temperature to 25-30° C. and maintain such temperature for 1 h. After the reaction is complete, the product is turbid. The concentration of free fatty acid salt in the product is measured at 5.8% with HPLC, and the conversion rate is calculated as 70% by the acyl chloride.

Example 3

Preparation of Sodium Lauroyl Glutamate

Place 290 g sodium glutamate aqueous solution in a reactor (25% sodium glutamate, pH value: 12, temperature: 20° C.). Add 125 g lauroyl chloride in a dropping funnel, wherein the molar ratio of the acyl chloride to glutamic acid is 1:0.75. Slowly add the acyl chloride dropwise, and use 30% sodium hydroxide solution to adjust the pH value of the material in the reactor and maintain the pH value at 10 to 11. After the acyl chloride is added dropwise to 75%, immediately add 188 g sodium sarcosinate aqueous solution with a concentration of 15%, wherein the molar ratio of the sodium sarcosinate to the acyl chloride is 0.35:1; and slowly increase the reaction temperature to 25-30° C. and maintain such temperature for 1 h. After the reaction is complete, the product is clear and transparent. The concentration of free fatty acid salt in the product is measured as 2.7% with HPLC, and the conversion rate is calculated as 86% by the acyl chloride.

Example 4

Preparation of Sodium C12/C14 Acyl Glutamate

Under similar conditions as Example 1, the coconut acid chloride is substituted with C12/C14 mixed fatty acyl chloride. The molar ratio of the acyl chloride versus glutamic acid versus glycine is 1:1:0.1. The sodium hydroxide is substituted with KOH. After the reaction is complete, the product is slightly turbid. The concentration of free fatty acid salt in the product is measured as 4.1% with HPLC, and the conversion rate is calculated as 80% by the acyl chloride.

Example 5

Sodium Oleoyl Glutamate

With similar method as Example 1, the coconut acid chloride is substituted with oleoyl chloride, and the glycine is substituted with β-lactamic acid. The molar ratio of the acyl chloride versus glutamic acid versus lactamic acid is 1:0.9:0.2. After the reaction is complete, the product is clear and transparent. The concentration of free fatty acid salt in the product is measured as 5.6% with HPLC, and the conversion rate is calculated as 78% by the acyl chloride.

Example 6

Application of Sodium Cocoyl Glutamate

The N-acyl acidic amino acid salt prepared by the method herein can be used directly. For example, the product in Example 1 can be used in the following facial cleanser formulation:

| | |
|---|---|
| Sodium cocoyl glutamate | 25% |
| cocoamidopropyl betaine | 20% |
| Propylene glycol | 15% |
| butylene glycol | 5% |
| Linoleamidopropyl PG-dimonium Chloride Phosphate | 1% |
| Talc powder | 1% |
| Hydroxyethylcellulose | 1.5% |
| Citrate acid | Adjust pH value to 5.5 |
| Water | To 100%. |

The invention claimed is:

1. A method of preparing an N-acyl acidic amino acid or a salt thereof, comprising: subjecting a fatty acid chloride and an amino acid to an amidation reaction under a basic condition, characterized in that, the amidation reaction uses water as a solvent, an acidic amino acid or a salt thereof as a main reactant and a small amount of a neutral amino acid or a salt thereof as an auxiliary reactant; while stirring, first adding the fatty acid chloride gradually into an aqueous solution of the acidic amino acid or a thereof; adding a base to adjust the pH value of the reaction solution; after a certain amount of the fatty acid chloride has been added, adding an aqueous solution of the neutral amino acid or a salt thereof, and continuing to add the fatty acid chloride gradually until the addition is finished and stirring to maintain the reaction.

2. The method of claim 1, wherein the molar ratio of the acidic amino acid to the fatty acid chloride to the neutral amino acid is 0.6-1.3:1:0.01-0.5.

3. The method of claim 2, wherein the molar ratio of the acidic amino acid to the fatty acid chloride to the neutral amino acid is 0.8-1.0:1:0.1-0.3.

4. The method of claim 1, wherein the neutral amino acid is added when the added fatty acid chloride reaches 40% to 100% of its total amount.

5. The method of claim 4, wherein the neutral amino acid is added when the added fatty acid chloride reaches 60% to 100% of its total amount.

6. The method of claim 1, wherein pH of the reaction solution is maintained at 9 to 14.

7. The method of claim 1, wherein the reaction temperature is 5° C. to 50° C.

8. The method of claim 1, wherein the carbon chain length of the fatty acid chloride is C6 to C22, or any combination thereof.

9. The method of claim 8, wherein the carbon chain length of the fatty acid chloride is C8 to C18.

* * * * *